United States Patent [19]

Duve

[11] Patent Number: 5,531,965
[45] Date of Patent: Jul. 2, 1996

[54] APPARATUS FOR DETERMINING DECOMPOSABLE ORGANIC CARBON COMPOUNDS PRESENT IN A GASEOUS PHASE

[75] Inventor: Hans Duve, Duelmen, Germany

[73] Assignee: HULS Aktiengesellschaft, Marl, Germany

[21] Appl. No.: 487,892

[22] Filed: Jun. 7, 1995

Related U.S. Application Data

[60] Division of Ser. No. 284,394, Jun. 1, 1994, which is a continuation-in-part of Ser. No. 492,970, Mar. 13, 1990, abandoned.

[30] Foreign Application Priority Data

Mar. 21, 1989 [DE] Germany ............... 39 09 227.5

[51] Int. Cl.[6] ................................. G01N 31/12
[52] U.S. Cl. ................. 422/80; 422/78; 422/82.02; 436/146
[58] Field of Search ............... 422/78–80, 82.02; 436/146

[56] References Cited

U.S. PATENT DOCUMENTS

| | | |
|---|---|---|
| 3,958,941 | 5/1976 | Regan . |
| 4,230,665 | 10/1980 | Huber . |
| 4,248,598 | 2/1981 | Blunck . |
| 4,277,438 | 7/1981 | Ejzak . |
| 4,293,522 | 10/1981 | Winkler . |
| 4,622,306 | 11/1986 | Duve . |
| 4,666,860 | 5/1987 | Blades et al. . |
| 4,749,657 | 6/1988 | Takahashi et al. . |
| 4,769,217 | 9/1988 | Sienkiewicz et al. . |
| 4,775,634 | 10/1988 | Sienkiewicz . |
| 5,244,811 | 9/1993 | Matthews ............... 436/146 |
| 5,271,900 | 12/1993 | Morita . |
| 5,292,666 | 3/1994 | Fabinski et al. . |

FOREIGN PATENT DOCUMENTS

| | | |
|---|---|---|
| 2408139 | 6/1979 | France . |
| 3223167 | 12/1983 | Germany . |

OTHER PUBLICATIONS

Poirier, S. J. et al. "A New Approach to the Measurement of Organic Carbon" American Laboratory (1978).

*Primary Examiner*—Jeffrey R. Snay
*Attorney, Agent, or Firm*—Longacre & White

[57] ABSTRACT

The content of decomposable organic carbon compounds present in a gaseous phase is determined down to the parts per billion ($10^{-9}$) range and in special cases down to the parts per trillion ($10^{-12}$) range. The gaseous sample material being tested is introduced into a limited quantity of water wherein the organic compounds are photolytically decomposed. The decomposition products are ascertained in the carrier gas and/or in the limited quantity of water.

7 Claims, 2 Drawing Sheets

APPARATUS FOR DETERMINING DECOMPOSABLE ORGANIC CARBON COMPOUNDS PRESENT IN A GASEOUS PHASE

This is a divisional of application Ser. No. 08/284,394, filed Jun. 1, 1994, which is a Continuation-In-Part of U.S. patent application Ser. No. 07/492,970, filed 13 Mar. 1990, now abandoned.

BACKGROUND OF THE INVENTION

1. Field of the Invention

The invention concerns a method for determining continuously the presence of decomposable organic compounds in a gaseous phase.

The object of the invention is to show in a simple manner the presence, even in very low concentrations, of organic compounds in a gas phase. Both the content of organically bound carbon and the content of organically bound heteroatoms (for instance chlorine, fluorine) in a gas phase are detectable. Such monitoring is required, for example, of gases when it is surmised that there are compounds within them that might interfere. The gas flows to be checked may be partial amounts of a large volume of gas (for instance ambient room air, oxygen, inert gases, exhaust gases).

2. Description of the Related Art

The state of the art of measuring the content of organic carbon in water and aqueous solutions may be ascertained by reference to U.S. Pat. Nos. 3,958,941 and 4,769,217, the disclosures of which are incorporated herein by reference.

U.S. Pat. No. 3,958,941 discloses a discontinuous procedure for determining organically bound carbon in an aqueous solution. An aqueous sample is added to a carrier liquid such as pure water, the mixture is circulated through a photo-reactor and exposed to ultraviolet light (i.e. a uv reactor). The carbon dioxide ($CO_2$) generated in the decomposition of the organic compounds is expelled from the carrier liquid, then the carbon dioxide is dissolved again in a sealed, partial volume of the carrier liquid and its presence therein is determined by means of a conductivity measurement. Upon termination of the test on a sample, the liquid contents of the two partial volumes are continuously passed through an ion exchanger and are regenerated thereby into pure water. This procedure is restricted to testing aqueous single samples, and only the volatile $CO_2$ dissociation product produced from the organic compounds is determined as being present.

West German patent 32 23 167 describes a procedure for testing water containing dissociable carbon compounds. An aqueous-sample flow is passed continuously through an ultraviolet reactor and the non-volatile compounds produced from the organic compounds being present are determined in the aqueous-sample flow by means of conductivity measurements when the sample leaves the ultraviolet reactor. In this test procedure, the non-volatile decomposition products from organic compounds contained in an aqueous-sample flow are also determined.

SUMMARY OF THE INVENTION

Accordingly, there is a need to find a method whereby organic compounds contained in a gas phase can be completely determined, together with the decomposition products free of carbon, in simple manner and with great sensitivity.

This need is met by the method of the present invention wherein the gaseous phase to be tested is conducted through a limited quantity of water. The organic carbon compounds contained in the gaseous phase are irradiated in an ultraviolet reactor containing at least part of the limited quantity of water, and the decomposition products formed in the decomposition of the organic carbon compounds are determined.

This method is furthermore characterized in that the decomposition products formed in the decomposition of the organic carbon compounds in the limited quantity of water are shown to be present by means of an ion detector.

The ultraviolet reactor is filled with a limited quantity of water. This quantity of water is recirculated by a pump in an external circuit. Accordingly, the circulating water constantly passes through the ultraviolet reactor and the organic compounds contained in the circulating water are photochemically decomposed and ionized. The ion content of the circulating water is determined by an ion detector in the circulating water leaving the ultraviolet reactor. The circulating water is passed through an ion exchanger before being fed back into the ultraviolet reactor, then the ions contained in the circulating water are continuously removed by that exchanger. A low and constant measurement value at the ion detector behind the ultraviolet reactor indicates that the circulating water is free of decomposable organic compounds and of inorganic ions. A gaseous phase being investigated is introduced into this volumetrically defined circulating water preparation. The location at which the gaseous phase is introduced into the circulating water greatly affects the resulting measurement taking place in the presence of organic compounds in the gaseous phase.

The gaseous phase to be tested is bubbled into the lower or upper part of the ultraviolet reactor through the water circulating therein and constantly flowing therethrough. The gaseous phase exits at the upper or lower part of the ultraviolet reactor. The circulating water is passed through an ion detector, passed through a reservoir for the circulating water in the circuit, and fed back by a pump into the circuit through an ion exchanger into the lower part of the ultraviolet reactor. The organic compounds introduced by way of the gaseous phase into the ultraviolet reactor are converted by ultraviolet irradiation into carbon dioxide and possibly into non-carbonaceous decomposition products. The non-carbonaceous decomposition products (for instance ions of chloride, fluoride, etc.) remain totally in the circulating water and are shown to be present using an ion detector or in another ion sensing manner. The $CO_2$ content of the circulating water at the discharge of the ultraviolet reactor depends upon a variety of factors.

Preferably the gaseous phase introduced into the ultraviolet reactor is free of $CO_2$, or $CO_2$ is eliminated by means of a $CO_2$ adsorber before introduction. Thereby, the $CO_2$ produced in the decomposition of the organic compounds is removed almost entirely from the circulating water. Suitable $CO_2$ adsorbers are soda lime and soda asbestos. When granular soda lime or soda lime wafers are used as $CO_2$ adsorbers, then they are appropriately previously humidified with water. This one-time humidification prevents adsorbing organic compounds from the carrier gas. This property of the soda lime wafers surprisingly remains conserved following drying in the carrier-gas flow.

Accordingly, the gaseous phase fulfills the following functions:

it introduces the organic compounds to be ascertained into the ultraviolet reactor circulating water before this water is passed through the ion detector, and it evacuates the carbon dioxide produced in the decomposition of the organic compounds from the ultraviolet reactor circulating water before this water is passed through the ion detector.

The $CO_2$ generated in the decomposition of the organic compounds is ascertained in the gas phase exiting the ultraviolet reactor by means of a $CO_2$ detector.

When a constant quantity of decomposable organic compounds containing hetero-atoms is introduced per unit time through the gaseous phase into the water in the ultraviolet reactor, the proportion of non-carbonaceous decomposition products in the ultraviolet reactor is increased by decreasing the quantity per unit time of circulating water made to pass through the ultraviolet reactor. This results in an enrichment effect. Contrary to the enrichment of non-carbonaceous decomposition products in the ultraviolet reactor water, the $CO_2$ generated by the decomposition of the organic compounds is continuously expelled from the ultraviolet reactor water, however its presence in the gas phase leaving the ultraviolet reactor can be shown as a differential value by means of a $CO_2$ detector.

When the gas phase to be tested is passed through the water in the reservoir for the circuit, all the compounds present in the gas phase dissolve proportionately to their distribution coefficients (liquid phase/gaseous phase) in the water. A dynamic equilibrium is achieved for each ingredient of the gas phase in the reservoir water. When the circulating water leaving the reservoir is subsequently passed through an ion exchanger, all ion-forming components (for instance $CO_2$, $NH_3$, HCl, etc.) from the gas phase dissolved in the circulating water are removed before the water passes through the ultraviolet reactor. All products arising from the decomposition of the organic compounds remain in the circulating water and may be ascertained using an ion detector present in the circulating water after the ultraviolet reactor.

When the gas phase being tested contains compounds in aqueous solutions forming ions without ultraviolet irradiation, and when these compounds are wholly removed from the gas phase as it is passed through the reservoir, then it may be advantageous to pass the gas phase exiting the reservoir through the ultraviolet reactor water. In this case again it is possible to show the presence of the decomposition products in the gas phase leaving the ultraviolet reactor and in the circulating water after the ultraviolet reactor.

In every case the circulating water leaving the ultraviolet reactor can be made to pass through a selective ion exchanger before ion-determination by an ion detector. Specific types of ions can then be removed from the circulating water before analysis.

When organic compounds are surmised to be present in a liquid phase such that they can be removed from this phase by passing a flow carrier gas therethrough, the flow of carrier gas with the organic compounds can be subsequently stripped from the liquid phase and introduced as a gaseous sample substance into a limited quantity of water for testing. It may be advantageous to adjust the pH value of the liquid phase before the flow of carrier gas is passed through it by adding acid or lye in such a manner that any inorganic evaporatable compounds present in the liquid phase (for instance $CO_2$, $NH_3$, etc.) are converted into compounds which no longer can merge into the flow of the carrier gas. This takes place above a pH value of 8.3.

Preferably the flow of carrier gas is air free of carbonaceous substances. However, a carrier gas free of molecular oxygen, preferably nitrogen, or a noble gas such as helium or argon, may be advantageous.

DETAILED DESCRIPTION OF THE DRAWINGS

Figure 1:
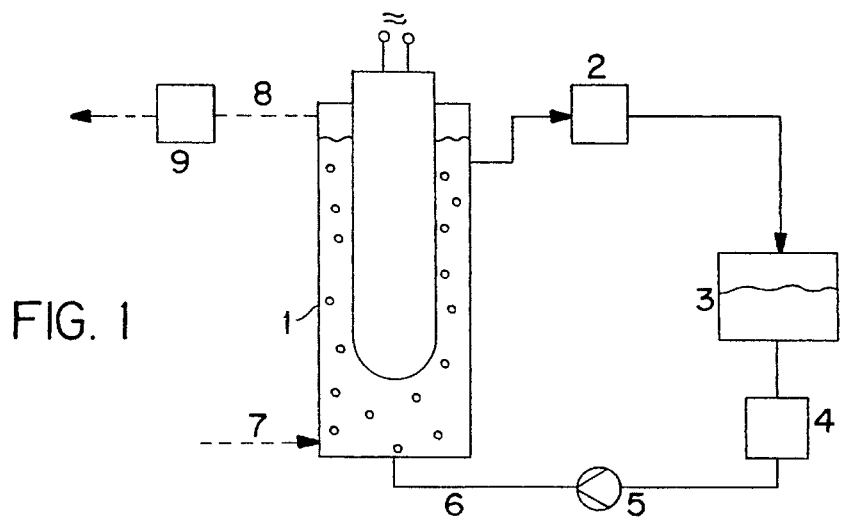
FIG. 1 is a flow diagram of apparatus for testing carbon compounds in a gas flow where the gas flow is conducted through the ultraviolet reactor.

In FIG. 1, a water circuit consists of an ultraviolet reactor 1, ion detector 2, reservoir 3, ion exchanger 4 and circulation pump 5. The circulating water is constantly circulated through a circulation conduit 6. A gas flow to be tested is bubbled through a gas feed line 7 into the lower part of the ultraviolet reactor 1 and into the water therein. The gas flow leaves the ultraviolet reactor 1 through a gas discharge 8 and, where called for, is passed through a $CO_2$ detector 9. The organic compounds entrained in the gas flow through the ultraviolet reactor 1 are decomposed into $CO_2$ and possibly also into non-carbonaceous products. The $CO_2$ generated together with the gas flow passed through the ultraviolet reactor water is completely removed from this water and can be shown as present in the gas flow leaving the ultraviolet reactor 1 by detector 9. The non-volatile decomposition products are determined in the circulating water leaving the ultraviolet reactor using an ion detector 2. The separation effect can be reinforced by extending the dwell-time of the circulating water in the ultraviolet reactor 1. In that case, the ion detector 2 is advantageously used directly on the irradiated water of the ultraviolet reactor 1. The circulating water leaving the ion detector 2 passes through the reservoir 3 and then through an ion exchanger 4, whereby all ionogenic compounds contained in the circulating water are removed. After the ion exchanger 4, the ion-free circulating water is moved by the pump 5 into the lower part of the ultraviolet reactor 1.

Figure 2:
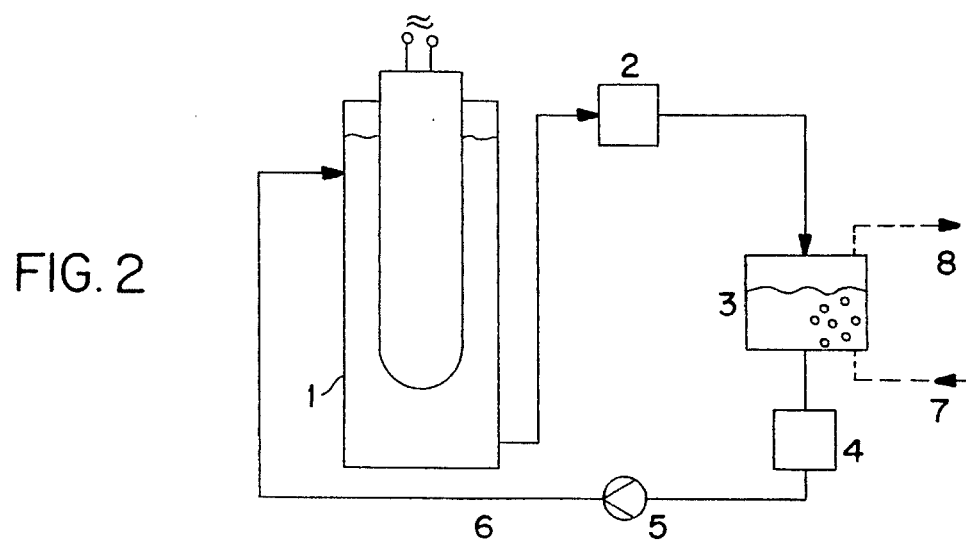
FIG. 2 is a modification of the flow diagram of FIG. 1 wherein the gas flow is conducted through the reservoir.

The design of the water circuit of FIG. 2 is similar to that of FIG. 1, but the gas flow to be tested is bubbled through a gas feed line 7 into the circulating water present in the reservoir 3. In this case, the circulating water enters the reactor 1 at its top and leaves the reactor 1 at its bottom. The gas flow leaves the reservoir 3 through a gas discharge line 8. In relation to the equilibria of solution, the ingredients of the supplied gas flow dissolve in the circulating water of the reservoir 3. The dissolved ionizing ingredients (for instance $CO_2$) from the gas flow are removed by the ion exchanger 4 from the circuit water. Where called for, an ion detector may be used to ascertain the presence of ions before the ion exchanger 4. All the non-ionogenic ingredients dissolved in the circulating water are moved together with the water into the ultraviolet reactor 1. The ionogenic decomposition products generated by irradiating the organic compounds pass through the ion detector 2 behind the ultraviolet reactor and are determined there. When a selective ion exchanger is crossed before the ion detector 2, which illustratively may be a cell measuring conductivity or an ion-selective electrode, then specific kinds of ions may be removed from the circulating water before measurement. The circulating water is fed back through the reservoir 3 into the ion exchanger 4 and therein is freed of all ionogenic ingredients. When the gas flow being tested lacks ingredients forming ions in the absence of ultraviolet irradiation, the ion exchanger 4 may also be mounted directly following the ion detector 2.

Figure 3:
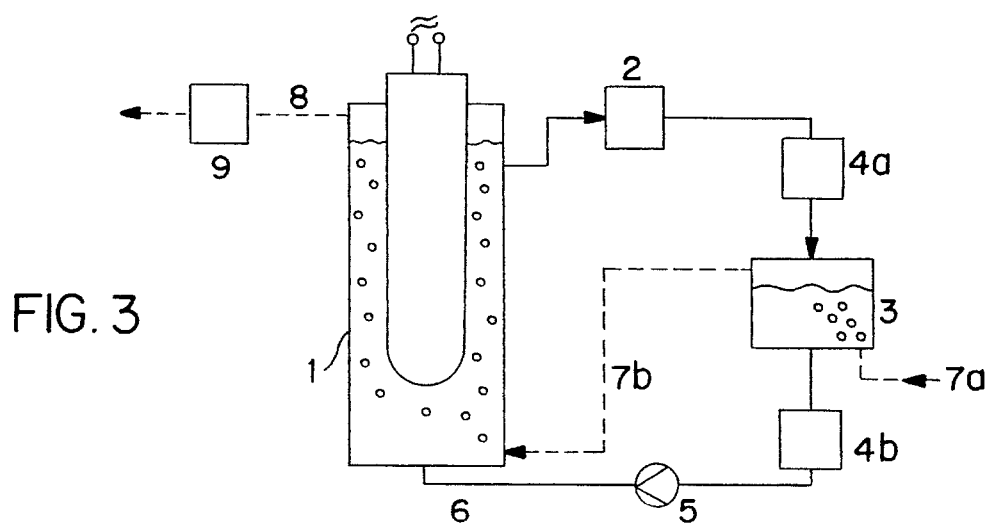
FIG. 3 is another embodiment of the flow diagram of FIG. 1 wherein the gas flow is passed through the reservoir and then through the ultraviolet reactor.

In FIG. 3, the gas flow to be tested, following introduction into the water of the reservoir through conduit 7a, is fed through conduit 7b into the water of the ultraviolet reactor 1. The gas flow exits the ultraviolet reactor 1 through conduit 8 and may be made to pass through a $CO_2$ detector 9 to determine the presence of the $CO_2$ produced in the decomposition of the organic compounds. The ionogenic compounds remaining in the circulating water after the ultraviolet reactor 1 are determined by the ion detector 2 and then are removed from the circulating water by ion exchanger 4a. When the gas phase introduced into the reservoir water also contains ingredients which in aqueous solution form ions, and of which the solubility equilibrium practically is entirely on the side of the aqueous solution (for instance hydrogen chloride), then these may be removed from the gas phase in the reservoir water. These ionogenic ingredients now dissolved in the circulating water are removed in the ion exchanger 4b (possibly upon detection) before this circulating water is introduced into the ultraviolet reactor.

The gas flows to be tested according to the present invention may be obtained from the sources shown in FIGS. 4 through 7, for example.

Figure 4:
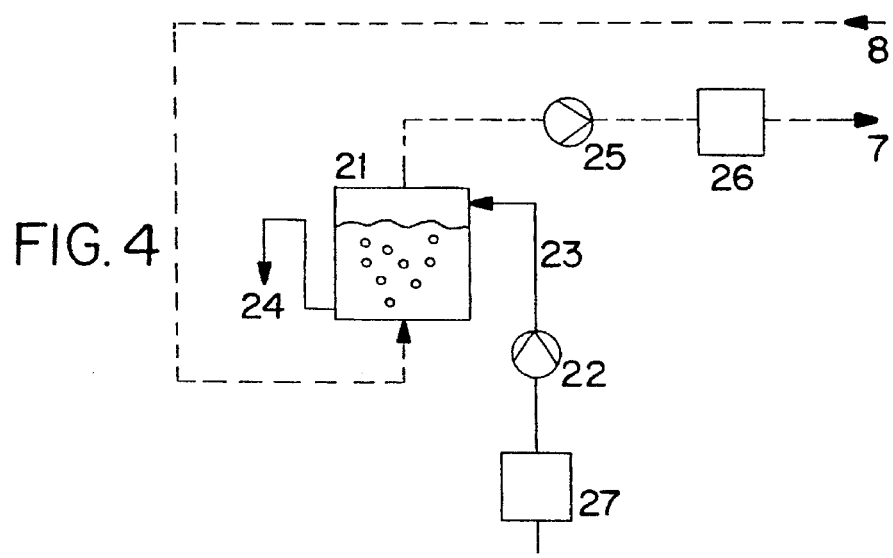
FIG. 4 is a flow diagram of an apparatus for the production of a gas phase for testing in the apparatus of FIGS. 1–3.

In FIG. 4, a liquid phase is supplied by means of a pump 22 and through a conduit 23 to a phase exchanger 21. The liquid phase exits through the goose-neck discharge 24 from the phase exchanger 21. The gas flow exiting from the ultraviolet reactor 1 through the gas evacuation conduit 8 (FIGS. 1 and 3) or from the reservoir 3 (FIG. 2) passes into the lower part of the phase exchanger 21 and there bubbles through the liquid. The gas flow is evacuated from the upper part of the phase exchanger 21 by a pump 25, and is passed through the gas feed line 7 into the ultraviolet reactor 1 or the reservoir 3. After passing through the phase exchanger 21, if the gas flow contains carbon dioxide, it may be advantageous to remove this ingredient by a $CO_2$ adsorber 26. This $CO_2$ adsorber may be dropped when the pH value of the liquid phase is so adjusted in a container 27 (prior to this phase being added to the phase exchanger 21), that the gas flow passing through the phase exchanger 21 is incapable of expelling ion-forming compounds from the liquid phase in the absence of ultraviolet irradiation.

Figure 5:
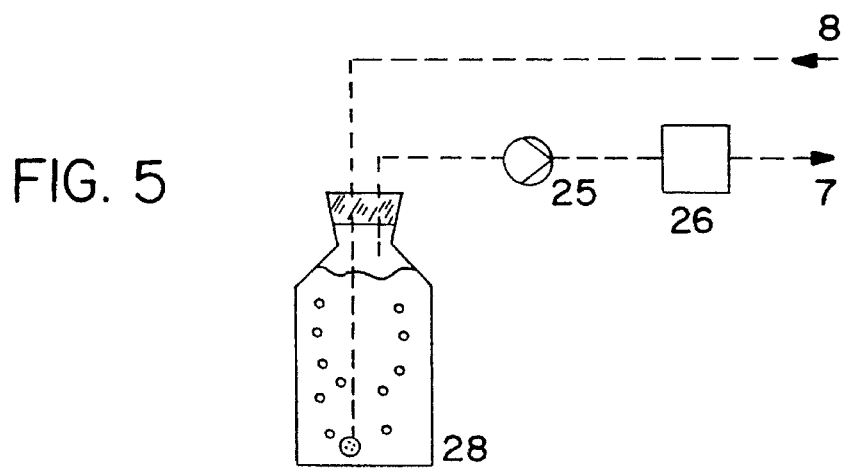
FIG. 5 is a flow diagram of another embodiment of the apparatus for the production of a gas phase for testing in the apparatus of FIGS. 1–3 wherein recirculated gas is bubbled into a liquid sample in a closed container.

A liquid phase is shown in FIG. 5 in a closed vessel 28. The gas flow fed back through the gas evacuation conduit 8 is bubbled in at the bottom of the vessel 28 into the liquid phase, whereas at the upper part of the vessel 28 it is evacuated by means of the pump 25, and then is moved through the gas supply conduit 7. As necessary, a $CO_2$ adsorber 26 may be placed in the gas supply conduit 7 prior to the ultraviolet reactor 1 or the reservoir 3.

Figure 6:
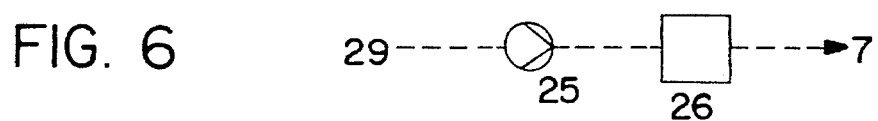
FIG. 6 is a flow diagram of an embodiment which directly collects a gas phase to be tested in the apparatus of FIGS. 1–3.

In FIG. 6, a pump 25 sucks in a gas flow through the conduit 29. The gas flow is passed over a $CO_2$ adsorber 26 and is moved through the gas supply line 7 into the ultraviolet reactor 1 or the reservoir 3. In this case, the gas flow leaving the subsequent measurement apparatus through the conduit 8 is discarded.

Figure 7:
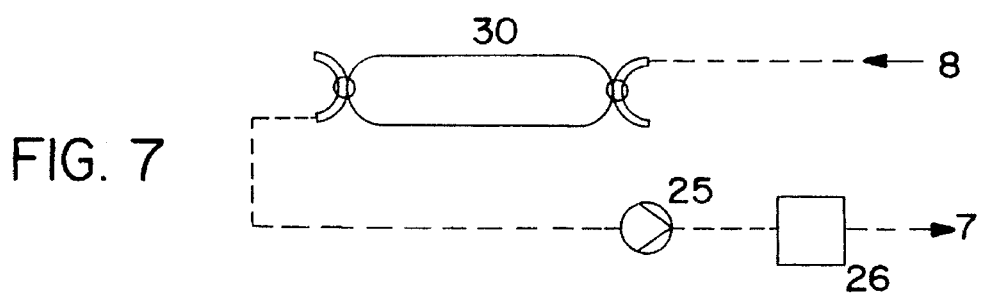
FIG. 7 is a flow diagram of an embodiment of a gas generator using a balloon.

A gas sample may also be present within a gas balloon 30 as shown in FIG. 7. The gas flow fed back through the gas evacuation conduit 8 is drawn by the pump 25 through the gas balloon 30 and is moved, where called for through a $CO_2$ adsorber 26, through the gas supply line 7 to the ultraviolet reactor 1 or to the reservoir 3.

The method of the invention offers the following advantages:

gas flows can be tested continuously in simple manner with great sensitivity for organic ingredients;

the method ascertains the presence of all decomposition products, carbonaceous and non-carbonaceous, from the organic compounds;

the total organic carbon content (TOC) of a gas flow can be determined in continuous manner;

non-volatile ionogenic decomposition products (for instance chloride ions from chlorinated hydrocarbons) can be enriched in the ultraviolet reactor. As a result and illustratively, the determination limit for chlorinated hydrocarbons present in a gas phase is in the ppt range (ppt=$10^{-12}$);

the water of extremely high purity required by the analysis as a solvent, a transporting agent and a reagent is constantly available on account of operation by circulation; and, the apparatus can be calibrated provided a solution is used of which the kind and concentration of the carbon compounds contained therein are known and that either the solution is introduced into the limited quantity of water or, as shown in FIGS. 4 and 5, the solution is crossed by a flow of carrier gas which subsequently is tested in an apparatus such as shown in FIGS. 1 through 3.

The present invention is elucidated below by means of the following Examples:

EXAMPLES

In the following examples abbreviations are used as follows:

ppb=parts per billion=$10^{-9}$

CHC=chlorinated hydrocarbons $\mu S/cm$=micro-Siemens per centimeter as the unit of specific conductivity Example 1

Testing an aqueous phase having a known content of trichloro-methane. The apparatus shown in FIG. 1 is used in this test. The determination of $CO_2$ in the carrier gas flow (air being free of $CO_2$) leaving the ultraviolet reactor is dropped. The gas flow fed to the ultraviolet reactor is prepared by the apparatus described in relation to FIG. 4. The aqueous phase to be tested (drinking water, free of CHC) is taken from a reservoir (omitted from FIG. 4) and is pumped at a rate of 10 liter/hr through the phase exchanger (300 ml capacity). The gas flow (100 liter/hr) passing through the phase exchanger is passed over a $CO_2$ adsorber (500 ml capacity) before being introduced into the ultraviolet reactor. Soda lime wafers with indicator (#6839, Merck, Darmstadt) are used as the $CO_2$ adsorbents. Before being placed in the $CO_2$ adsorption container, the soda lime wafers are first rid of any dusty soda lime they contain and then are humidified with water.

The ultraviolet reactor (water capacity=50 ml) is equipped with a low-pressure mercury vapor lamp of 25 watts power. The circulating water in the apparatus of FIG. 1 moves through a double bed ion exchanger (capacity=30 ml, cation exchanger, type Lewatit M 600 MB, Bayer mfr) before being introduced into the ultraviolet reactor. A temperaturecompensated conductivity measuring cell is used as the ion detector after the ultraviolet reactor.

The flow of the circulating water is raised stepwise from 0.18 liter/hr to 3.0 liter/hr, and at each adjustment, the pertinent conductivity of the circulating water behind the ultraviolet reactor is measured. Throughout the entire range of the flow, a conductivity of 0.1 μS/cm was ascertained in the circulating water. Accordingly, a defined initial state was obtained in the apparatus composed of that shown in FIGS. 1 and 4 (reservoir omitted).

Thereupon, 30 ppb of trichloro-methane is dissolved in the tested water of the reservoir (omitted from FIG. 4). The flow of the circulating water through the ultraviolet reactor again is varied stepwise and the associated conductivity is measured. The following measured values as a function of the flow were obtained:

| Flow through the ultraviolet reactor | |
| --- | --- |
| flow (lit/h) | conductivity (μS/cm) |
| 3.9 | 0.37 |
| 1.46 | 0.54 |
| 0.84 | 0.85 |
| 0.65 | 1.00 |
| 0.18 | 2.80 |

When the flow of the circulating water is reduced, and no other conditions are changed, the chloride ions produced from the decomposition of trichloro-methane are enriched in the ultraviolet reactor water and increase the magnitude of the measured effect.

Example 2

Testing an aqueous phase with known, different contents of trichloro-methane.

The test of Example 1 is repeated but the flow of circulating water through the ultraviolet reactor is set to a constant value of 0.2 liters/hr. In each test, 3 ppb, 6 ppb and 9 ppb of trichloro-methane are dissolved in the reservoir-water to be tested before this water is passed through the phase exchanger. A measurement was taken of the particular conductivity of the circulating water after the ultraviolet reactor. The following results were found as a function of the trichloro-methane concentration:

| trichloro-methane concentration, ppb | conductivity μS/cm |
| --- | --- |
| 0 | 0.20 |
| 3 | 0.44 |
| 6 | 0.67 |
| 9 | 0.91 |

The conductivity of the circulating water after the ultraviolet reactor increases in proportion to the trichloro-methane concentration in the water being tested.

I claim:

1. An apparatus for determining decomposable organic carbon compounds present in a gaseous phase, comprising;

a decomposition reactor containing an ultraviolet lamp;

a closed aqueous circuit including said decomposition reactor, a circulation pump, at least one ion detector, and an ion exchanger; wherein said circulation pump establishes a continuous liquid flow in said closed aqueous circuit through said reactor, said at least one ion detector and said ion exchanger, sequentially;

a gas feed line feeding the gaseous phase to be tested into said aqueous circuit, and a gas discharge line discharging the gaseous flow leaving said aqueous circuit.

2. The apparatus of claim 1, wherein said aqueous circuit feeds water to a bottom of said decomposition reactor and removes said water from a top of said decomposition reactor.

3. The apparatus of claim 2, further comprising:

a second ion exchanger in said circuit;

said gas feed line introducing the gaseous phase to be tested into water running through a reservoir in said aqueous circuit; and said gas discharge line taking-off the gaseous phase from said reservoir;

wherein said water flows into said decomposition reactor then into one of said at least one ion detectors then into said ion exchanger then into said water reservoir then into said second ion exchanger then into said decomposition reactor.

4. The apparatus of claim 2, further comprising:

a second ion exchanger in said circuit;

said gas feed line introducing the gaseous phase to be tested into water running through a reservoir in said aqueous circuit;

a connection conduit connecting said reservoir to said bottom of said decomposition reactor; and said gas discharge line taking-off said gaseous phase from said decomposition reactor;

wherein said water flows into said decomposition reactor then into one of said at least one ion detectors then into said ion exchanger then into said water reservoir then into said second ion exchanger then into said decomposition reactor.

5. The apparatus of claim 1, wherein said aqueous circuit feeds water to a top of said decomposition reactor and removes said water from a bottom of said decomposition reactor.

6. The apparatus of claim 5, further comprising:

a second ion exchanger in said circuit;

said gas feed line introducing the gaseous phase to be tested into water running through a reservoir in said aqueous circuit; and said gas discharge line taking-off the gaseous phase from said reservoir;

wherein said water flows into said decomposition reactor then into one of said at least one ion detectors then into said ion exchanger then into said water reservoir then into said second ion exchanger then into said decomposition reactor.

7. The apparatus of claim 5, further comprising:

a second ion exchanger in said circuit;

said gas feed line introducing the gaseous phase to be tested into water running through a reservoir in said aqueous circuit;

a connection conduit connecting said reservoir to said bottom of said decomposition reactor; and said gas discharge line taking-off said gaseous phase from said decomposition reactor;

wherein said water flows into said decomposition reactor then into one of said at least one ion detectors then into said ion exchanger then into said water reservoir then into said second ion exchanger then into said decomposition reactor.

* * * * *